United States Patent
Albert et al.

[11] Patent Number: 5,804,447
[45] Date of Patent: Sep. 8, 1998

[54] USE OF COMPOUNDS WHICH ABSORB AND/OR FLUORESCE IN THE IR REGION AS MARKERS FOR LIQUIDS

[75] Inventors: Bernhard Albert, Maxdorf; Juergen Kipper, Karlsruhe; Christos Vamvakaris, Kallstadt; Karin Heidrun Beck, Ludwigshafen; Gerhard Wagenblast, Weisenheim, all of Germany

[73] Assignee: BASF Aktiengesellschaft, Ludwigshafen, Germany

[21] Appl. No.: 844,861

[22] Filed: Apr. 23, 1997

Related U.S. Application Data

[63] Continuation of Ser. No. 562,789, filed as PCT/EP93/01830, Jul. 13, 1993, abandoned, which is a continuation of Ser. No. 367,315, Jan. 20, 1995, abandoned.

[30] Foreign Application Priority Data

| | | | |
|---|---|---|---|
| Jul. 23, 1992 | [DE] | Germany | 42 24 301.7 |
| Dec. 23, 1992 | [DE] | Germany | 42 43 776.8 |
| Dec. 23, 1992 | [DE] | Germany | 42 43 774.1 |

[51] Int. Cl.$^6$ .................................. G01N 33/22
[52] U.S. Cl. ................. 436/56; 436/172; 436/60; 436/30; 436/27
[58] Field of Search ................. 436/22–26, 30, 436/56–57, 60, 172, 178

[56] References Cited

U.S. PATENT DOCUMENTS

| | | |
|---|---|---|
| 3,023,186 | 9/1962 | Geiger et al. . |
| 3,484,467 | 12/1969 | Susi et al. . |
| 4,009,008 | 2/1977 | Orelup .......... 44/59 |
| 4,209,302 | 6/1980 | Orelup .......... 44/59 |
| 4,659,679 | 4/1987 | Rhyne .......... 436/56 |
| 4,735,631 | 4/1988 | Orelup .......... 414/59 |
| 4,990,649 | 2/1991 | Schrott et al. . |
| 5,061,596 | 10/1991 | Albert et al. . |
| 5,084,592 | 1/1992 | Schroh . |
| 5,397,817 | 3/1995 | Krutak et al. .......... 524/88 |
| 5,525,516 | 6/1996 | Krutak et al. . |

FOREIGN PATENT DOCUMENTS

| | | |
|---|---|---|
| A-155780 | 2/1985 | European Pat. Off. . |
| 358080 | 8/1989 | European Pat. Off. . |
| 464543 | 6/1991 | European Pat. Off. . |
| 2168372 | 12/1985 | United Kingdom . |
| 2220650 | 6/1989 | United Kingdom . |

OTHER PUBLICATIONS

Symposium on Modern Analytical Techniques for the Analysis of Petroleum, pp. 291–304, Aug. 25–30, 1991, Marilyn V. Reyes, "Derivative Spectroscopy As An Analytical Tool For Hydrocarbon Identification".

F.H. Noser, A.L. Thomas, "The Phthalocyanines", CRC Press, Inc. Boca Raton, Florida 33431 vols. I–II, table of contents only, No date provided.

J. Am. Chem. Soc. 1984, vol. 106, pp. 7404 to 7410.

*Primary Examiner*—Lyle A. Alexander
*Attorney, Agent, or Firm*—Oblon, Spivak, McClelland, Maier & Neustadt, P.C.

[57] ABSTRACT

Use of compounds from the class of the phthalocyanines, naphthalocyanines, nickel dithiolene complexes, aminium compounds of aromatic amines, methine dyes or azulenesquaric acid dyes which have their absorption maximum in the range from 600 to 1,200 nm and/or a fluorescence maximum in the range from 620 to 1,200 nm, as markers for liquids, a process for detecting markers in liquids, and a detector suitable for this purpose.

10 Claims, 1 Drawing Sheet

FIG. 1

USE OF COMPOUNDS WHICH ABSORB AND/OR FLUORESCE IN THE IR REGION AS MARKERS FOR LIQUIDS

This application is a continuation of application Ser. No. 08/562,789, filed on Nov. 27, 1995, now abandoned, which is a continuation of Ser. No. 08/367,315, filed on Jan. 20, 1995, abandoned, which was filed as International Application No. PCT/EP93/01830, on Jul. 13, 1993.

BACKGROUND OF THE INVENTION

1. Field of the Invention

The present invention relates to the use of compounds from the class of metal-free or metal-containing phthalocyanines, metal-free or metal-containing naphthalocyanines, nickel dithiolene complexes, aminium compounds of aromatic amines, methine dyes or azulenesquaric acid dyes which have their absorption maximum in the range from 600 to 1,200 nm and/or a fluorescence maximum in the range from 620 to 1,200 nm, as markers (tracers) for liquids, to a method for detecting markers in liquids, and to a detector suitable for this purpose.

2. Discussion of the Background

It is frequently necessary to mark liquids in order subsequently, for example when they are used, to re-detect the thus-marked liquids by means of suitable methods.

For example, heating oil can be differentiated from diesel oil in this way.

It is an object of the present invention to provide suitable compounds which are suitable as markers. The markers should have sufficiently strong absorption and/or fluorescence in the near infrared, so that detection of the absorption by means of conventional photometers which are sensitive in this range and/or of the fluorescence by means of conventional instruments after excitation with a suitable radiation source is possible.

SUMMARY OF THE INVENTION

We have found that this object is achieved by the compounds described in greater detail at the outset.

Metal-containing phthalocyanines or naphthalocynanines generally contain lithium (twice), magnesium, zinc, copper, nickel, VO, TiO or AlCl as the central atom.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawing wherein.

DETAILED DESCRIPTION OF THE PREFERRED EMBODIMENTS

Suitable phthalocyanines have, for example, the formula Ia where $Me^1$ is two hydrogen atoms, two lithium atoms or magnesium, zinc, copper, nickel, VO, TiO, AlCl or $Si(OH)_2$, at least 4 of the radicals $R^1$ to $R^{16}$, independently of one another, have the formula $W—X^1$ in which W is a chemical bond, sulfur, imino, $C_1$–$C_4$-alkylimino or phenylimino, and $X^1$ is $C_1$–$C_{20}$-alkyl, which may be interrupted by from 1 to 4 oxygen atoms in ether function or substituted by phenyl, or are adamantyl or substituted or unsubstituted phenyl, and any remaining radicals $R^1$ to $R^{16}$ are hydrogen, halogen, hydroxysulfonyl or $C_1$–$C_4$-dialkylsulfamoyl.

Other suitable phthalocyanines have, for example, the formula Ib where

$R^{17}$ and $R^{18}$ or $R^{18}$ and $R^{19}$ or $R^{19}$ and $R^{20}$ together in each case have the formula $X^2—C_2H_4—X^3$, in which one of the two radicals $X^2$ and $X^3$ is oxygen and the other is imino or $C_1$–$C_4$-alkylimino, and $R^{19}$ and $R^{20}$ or $R^{17}$ and $R^{20}$ or $R^{17}$ and $R^{18}$ independently of one another, are in each case hydrogen or halogen, and $Me^1$ is as defined above.

Suitable naphthalocyanines have, for example, the formula II where
$Y^1$, $Y^2$, $Y^3$, $Y^4$, $Y^5$, $Y^6$, $Y^7$ and $Y^8$, independently of one another, are each hydrogen, hydroxyl, $C_1$–$C_{20}$-alkyl or $C_1$–$C_{20}$-alkoxy, where the alkyl groups may each be interrupted by from 1 to 4 oxygen atoms in ether function and may be substituted by phenyl,
$Y^9$, $Y^{10}$, $Y^{11}$ and $Y^{12}$, independently of one another, are each hydrogen, $C_1$–$C_{20}$-alkyl or $C_1$–$C_{20}$-alkoxy, where the alkyl groups may each be interrupted by from 1 to 4 oxygen atoms in ether function, or are halogen, hydroxysulfonyl or $C_1$–$C_4$-dialkylsulfamoyl, and $Me^2$ is two hydrogen atoms, two lithium atoms, magnesium, zinc, copper, nickel, VO, TiO, AlCl or where
$Y^{17}$ and $Y^{18}$, independently of one another, are each hydroxyl, $C_1$–$C_{20}$-alkoxy, $C_1$–$C_{20}$-alkyl, $C_2$–$C_{20}$-alkenyl, $C_3$–$C_{20}$-alkenyloxy or $$O-\underset{\underset{Y^{21}}{|}}{\overset{\overset{Y^{20}}{|}}{Si}}-O-Y^{19}$$

in which $Y^{19}$ is $C_1$–$C_{20}$-alkyl, $C_2$–$C_{20}$-alkenyl or $C_4$–$C_{20}$-alkadienyl and $Y^{20}$ and $Y^{21}$, independently of one another, are each $C_1$–$C_{12}$-alkyl, $C_2$–$C_{12}$-alkenyl or as defined for $OY^{19}$ above.

Of particular interest here are naphthalocyanines of the formula II in which at least one of $Y^1$ to $Y^8$ is not hydrogen.

Suitable nickel dithiolene complexes have, for example, the formula III where
$L^1$, $L^2$, $L^3$ and $L^4$, independently of one another, are each $C_1$–$C_{20}$-alkyl, which may be interrupted by from 1 to 4 oxygen atoms in ether function, phenyl, $C_1$–$C_{20}$-alkylphenyl, $C_1$–$C_{20}$-alkoxyphenyl, where the alkyl groups may each be interrupted by from 1 to 4 oxygen atoms in ether function, or $L^1$ and $L^2$ and/or $L^3$ and $L^4$ in each case together are Suitable aminium compounds have, for example, the formula IV where
$Z^1$, $Z^2$, $Z^3$ and $Z^4$, independently of one another, are each $C_1$–$C_{20}$-alkyl, which may be interrupted by from 1 to 4 oxygen atoms in ether function, $C_1$–$C_{20}$-alkanoyl or where $Z^6$ is hydrogen, $C_2$–$C_{20}$-alkyl, which may be interrupted by from 1 to 4 oxygen atoms in ether function, or $C_1$–$C_{20}$-alkanoyl, $Z^7$ is hydrogen or $C_1$–$C_{20}$-alkyl, which may be interrupted by from 1 to 4 oxygen atoms in ether function, and $Z^8$ is hydrogen, $C_1$–$C_{20}$-alkyl, which may be interrupted by from 1 to 4 oxygen atoms in ether function, or halogen, and
$An^{\ominus}$ is the equivalent of an anion.

Suitable methine dyes have, for example, the formula V in which the rings A and B, independently of one another, may each be benzo-fused and/or substituted,

$E^1$ and $E^2$, independently of one another, are each oxygen, sulfur, imino, —C(CH$_3$)$_2$— or —CH=CH—, D is or where $E^3$ is hydrogen, $C_1$–$C_6$-alkyl, chlorine or bromine and $E^4$ is hydrogen or $C_1$–$C_6$-alkyl,
$Q^1$ and $Q^2$, independently of one another, are each phenyl, $C_5$–$C_7$-cycloalkyl, $C_1$–$C_{12}$-alkyl, which may be interrupted by from 1 to 3 oxygen atoms in ether function and may be substituted by hydroxyl, chlorine, bromine, carboxyl, $C_1$–$C_4$-alkoxycarbonyl, acryloyloxy, methacryloyloxy, hydroxysulfonyl, $C_1$–$C_7$-alkanoylamino, $C_1$–$C_6$-alkylcarbamoyl, $C_1$–$C_6$-alkylcarbamoyloxy or $G^{\ominus}(K)_3$, where G is nitrogen or phosphorus and K is phenyl, $C_5$–$C_7$-cycloalkyl or $C_1$–$C_{12}$-alkyl,
$An^{\ominus}$ is the equivalent of an anion, and n is 1, 2 or 3.

Suitable azulenesquaric acid dyes have, for example, the formula VI (VI)

where
J is $C_1$–$C_{12}$-alkylene,
$T^1$ is hydrogen, halogen, amino, hydroxyl, $C_1$–$C_{12}$-alkoxy, phenyl, substituted phenyl, carboxyl, $C_1$–$C_{12}$-alkoxycarbonyl, cyano, —$NT^7$—CO—$T^6$, —CO—$NT^6T^7$ or —O—CO—$NT^6T^7$, where $T^6$ and $T^7$, independently of one another, are each hydrogen, $C_1$–$C_{12}$-alkyl, $C_5$–$C_7$-cycloalkyl, phenyl, 2,2,6,6-tetramethylpiperidin-4-yl or cyclohexylamino-carbonyl, and
$T^2$, $T^3$, $T^4$ and $T^5$, independently of one another, are each hydrogen or $C_1$–$C_{12}$-alkyl, which may be substituted by halogen, amino, $C_1$–$C_{12}$-alkoxy, phenyl, substituted phenyl, carboxyl, $C_1$–$C_{12}$-alkoxycarbonyl or cyano, with the proviso that, if $T^5$ is hydrogen, the ring positions of the substituents J—$T^1$ and $T^4$ within an azulene ring may also be exchanged for one another on one or both azulene rings.

All the alkyl, alkylene and alkenyl radicals occurring in the above formulae may be either straight-chain or branched.

In the formulae Ia, II, III and IV, suitable $C_1$–$C_{20}$-alkyl radicals, which may be interrupted by from 1 to 4 oxygen atoms in ether function, are, for example, methyl, ethyl, propyl, isopropyl, butyl, isobutyl, sec-butyl, tert-butyl, pentyl, isopentyl, neopentyl, tert-pentyl, hexyl, 2-methylpentyl, heptyl, octyl, 2-ethyl-hexyl, isooctyl, nonyl, isononyl, decyl, isodecyl, undecyl, dodecyl, tridecyl, 3,5,5,7-tetramethylnonyl, isotridecyl (the above terms isooctyl, isononyl, isodecyl and isotridecyl are trivial names and originate from the alcohols obtained from the oxo synthesis—cf. in this respect Ullmanns Encyklopädie der technischen Chemie, 4th Edition, Volume 7, pages 215–217, and Volume 11, pages 435 and 436), tetradecyl, pentadecyl, hexadecyl, heptadecyl, octadecyl, nonadecyl, eicosyl, 2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 2- and 4-butoxybutyl, 3,6-dioxaheptyl, 3,6-dioxaoctyl, 4,8-dioxanonyl, 3,7-dioxaoctyl, 3,7-di-oxanonyl, 4,7-dioxaoctyl, 4,7-dioxanonyl, 4,8-dioxadecyl, 3,6,8-trioxadecyl, 3,6,9-trioxaundecyl, 3,6,9,12-tetraoxatridecyl and 3,6,9,12-tetraoxatetradecyl.

In the formulae I and II, suitable phenyl-substituted $C_1$–$C_{20}$-alkyl radicals are, for example, benzyl and 1- and 2-phenylethyl.

In the formulae II, III and IV, suitable $C_1$–$C_{20}$-alkoxy radicals, which may be interrupted by from 1 to 4 oxygen atoms in ether function, are, for example, methoxy, ethoxy, propoxy, isopropoxy, butoxy, isobutoxy, pentoxy, hexyloxy, heptyloxy, octyloxy, 2-ethylhexyloxy, isooctyloxy, nonyloxy, isononyloxy, decyloxy, isodecyloxy, undecyloxy, dodecyloxy, tridecyloxy, isotridecyloxy, tetradecyloxy, pentadecyloxy, hexadecyloxy, heptadecyloxy, octadecyloxy, nonadecyloxy, eicosyloxy, 2-methoxyethoxy, 2-ethoxyethoxy, 2-propoxyethoxy, 2-isopropoxyethoxy, 2-butoxyethoxy, 2- and 3-methoxypropoxy, 2- and 3-ethoxypropoxy, 2- and 3-propoxypropoxy, 2- and 3-butoxypropoxy, 2- and 4-methoxybutoxy, 2- and 4-ethoxybutoxy, 2- and 4-propoxybutoxy, 2- and 4-butoxybutoxy, 3,6-dioxaheptyloxy, 3,6-dioxaoctyloxy, 4,8-dioxanonyloxy, 3,7-dioxaoctyloxy, 3,7-dioxanonyloxy, 4,7-dioxaoctyloxy, 4,7-dioxanonyloxy, 4,8-dioxadecyloxy, 3,6,8-trioxadecyloxy, 3,6,9-trioxaundecyloxy, 3,6,9,12-tetraoxatridecyloxy and 3,6,9,12-tetraoxatetradecyloxy.

In the formula II, suitable phenyl-substituted $C_1$–$C_{20}$-alkoxy radicals are, for example, benzyloxy and 1- and 2-phenylethoxy.

In the formulae Ia, III and VI, suitable substituted phenyl radicals are, for example, phenyl which is substituted by $C_1$–$C_6$-alkyl, $C_1$–$C_6$-alkoxy, hydroxyl or halogen. In general, there may be from 1 to 3 substituents.

Halogen in the formulae Ib, II, IV and VI is, for example, fluorine, chlorine or bromine.

The radicals W in the formula Ia and $X^2$ and $X^3$ in the formula Ib are, for example, methylimino, ethylimino, propylimino, isopropylimino or butylimino.

The radicals $R^1$ to $R^{16}$ in the formula Ia and $Y^9$ to $Y^{12}$ in the formula II are, for example, dimethylsulfamoyl, diethylsulfamoyl, dipropylsulfamoyl, dibutylsulfamoyl or N-methyl-N-ethylsulfamoyl.

$C_2$–$C_{20}$-alkenyl and $C_4$–$C_{20}$-alkandienyl in the formula II are, for example, vinyl, allyl, prop-1-en-1-yl, methallyl, ethallyl, but-3-en-1-yl, pentenyl, pentadienyl, hexadienyl, 3,7-dimethylocta-1,6-dien-1-yl, undec-10-en-1-yl, 6,10-dimethylundeca-5,9-dien-2-yl, octadec-9-en-1-yl, octadeca-9,12-dien-1-yl, 3,7,11,15-tetramethylhexadec-1-en-3-yl or eicos-9-en-1-yl.

$C_3$–$C_{20}$-alkenyloxy in the formula II is, for example, allyloxy, methallyloxy, but-3-en-1-yloxy, undec-10-en-1-yloxy, octadec-9-en-1-yloxy or eicos-9-en-1-yloxy.

$Z^6$ in the formula IV is, for example, formyl, acetyl, propionyl, butyryl, isobutyryl, pentanoyl, hexanoyl, heptanoyl, octanoyl or 2-ethylhexanoyl.

If the rings A and/or B in the formula V are substituted, suitable substituents are, for example, $C_1$–$C_6$-alkyl, phenyl-$C_1$–$C_6$-alkoxy, phenoxy, halogen, hydroxyl, amino, $C_1$–$C_6$-mono- or dialkylamino or cyano. The rings are generally monosubstituted to trisubstituted.

The radicals $E^3$, $E^4$, $Q^1$ and $Q^2$ in the formula V are, for example, methyl, ethyl, propyl, isopropyl, butyl, isobutyl, sec-butyl, pentyl, isopentyl, neopentyl, tert-pentyl or hexyl.

The radicals $Q^1$ and $Q^2$ are furthermore, for example, hexyl, 2-methylpentyl, heptyl, octyl, 2-ethylhexyl, isooctyl, nonyl, isononyl, decyl, isodecyl, undecyl, dodecyl, cyclopentyl, cyclohexyl, 2-methoxyethyl, 2-ethoxyethyl, 2- or 3-methoxypropyl, 2- or 3-ethoxypropyl, 2-hydroxyethyl, 2- or 3-hydroxypropyl, 2-chloroethyl, 2-bromoethyl, 2- or 3-chloropropyl, 2- or 3-bromopropyl, 2-carboxyethyl, 2- or 3-carboxypropyl, 2-methoxycarbonylethyl, 2-ethoxycarbonylethyl, 2- or 3-methoxycarbonylpropyl, 2- or 3-ethoxycarbonylpropyl, 2-acryloyloxyethyl, 2- or 3-acryloyloxypropyl, 2-methacryloyloxyethyl, 2- or 3-methacryloyloxypropyl, 2-hydroxysulfonylethyl, 2- or 3-hydroxysulfonylpropyl, 2-acetylaminoethyl, 2- or 3-acetylaminopropyl, 2-methylcarbamoylethyl, 2-ethylcarbamoylethyl, 2- or 3-methylcarbamoylpropyl, 2- or 3-ethylcarbamoylpropyl, 2-methylcarbamoyloxyethyl, 2-ethylcarbamoyloxyethyl, 2- or 3-methylcarbamoyloxypropyl, 2- or 3-ethylcarbamoyloxypropyl, 2-(trimethylammonium)ethyl, 2-(triethylammonium)ethyl, 2- or 3-(trimethylammonium)propyl, 2- or 3-(triethylammonium)propyl, 2-(triphenylphosphonium)ethyl or 2- or 3-(triphenylphosphonium)propyl.

$An^\ominus$ in the formulae IV and V is derived, for example, from anions of organic or inorganic acids. Particular preference is given to, for example, methane-sulfonate, 4-methylbenzenesulfonate, acetate, trifluoroacetate, heptafluorobutyrate, chloride, bromide, iodide, perchlorate, tetrafluoroborate, nitrate, hexafluorophosphate and tetraphenylborate.

The radicals J in the formula VI are, for example, methylene, ethylene, 1,2- or 1,3-propylene, 1,2-, 1,3-, 2,3- or 1,4-butylene, pentamethylene, hexamethylene, heptamethylene, octamethylene, nonamethylene, decamethylene, undecamethylene or dodecamethylene.

The radicals $T^2$, $T^3$, $T^4$ and $T^5$ in the formula VI are, for example, methyl, ethyl, propyl, isopropyl, butyl, isobutyl, sec-butyl, tert-butyl, pentyl, isopentyl, neopentyl, tert-pentyl, 2-methylbutyl, hexyl, 2-methylpentyl, heptyl, octyl, 2-ethylhexyl, isooctyl, nonyl, isononyl, decyl, undecyl, dodecyl, fluoromethyl, chloromethyl, difluoromethyl, trifluoromethyl, trichloromethyl, 2-fluoroethyl, 2-chloroethyl, 2-bromomethyl, 1,1,1-trifluoroethyl, heptafluoropropyl, 4-chlorobutyl, 5-fluoropentyl, 6-chlorohexyl, cyanomethyl, 2-cyanoethyl, 3-cyanopropyl, 2-cyanobutyl, 4-cyanobutyl, 5-cyanopentyl, 6-cyanohexyl, 2-aminoethyl, 2-aminopropyl, 3-aminopropyl, 2-aminobutyl, 4-aminobutyl, 5-aminopentyl, 6-aminohexyl, 2-hydroxyethyl, 2-hydroxypropyl, 3-hydroxypropyl, 2-hydroxybutyl, 4-hydroxybutyl, 5-hydroxypentyl, 6-hydroxyhexyl, 2-methoxyethyl, 2-ethoxyethyl, 2-propoxyethyl, 2-isopropoxyethyl, 2-butoxyethyl, 2-methoxypropyl, 2-ethoxypropyl, 3-ethoxypropyl, 4-ethoxybutyl, 4-isopropoxybutyl, 5-ethoxypentyl, 6-methoxyhexyl, benzyl, 1-phenylethyl, 2-phenylethyl, 4-chlorobenzyl, 4-methoxybenzyl, 2-(4-methylphenyl) ethyl, carboxymethyl, 2-carboxyethyl, 3-carboxypropyl, 4-carboxybutyl, 5-carboxypentyl, 6-carboxyhexyl, methoxycarbonylmethyl, ethoxycarbonylmethyl, 2-methoxycarbonylethyl, 2-ethoxycarbonylethyl, 3-methoxycarbonylpropyl, 3-ethoxycarbonylpropyl, 4-methoxycarbonylbutyl, 4-ethoxycarbonylbutyl, 5-methoxycarbonylpentyl, 5-ethoxycarbonylpentyl, 6-methoxycarbonylhexyl or 6-ethoxycarbonylhexyl.

$T^1$ in the formula VI is, for example, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, isopentoxycarbonyl, neopentoxycarbonyl, tert-pentoxycarbonyl, hexyloxycarbonyl, heptyloxycarbonyl, octyloxycarbonyl, isooctyloxycarbonyl, nonyloxycarbonyl, isononyloxycarbonyl, decyloxycarbonyl, isodecyloxycarbonyl, undecyloxycarbonyl, dodecyloxycarbonyl, methoxy, ethoxy, propoxy, isopropoxy, butoxy, isobutoxy, pentoxy, hexyloxy, acetylamino, carbamoyl, mono- or dimethylcarbamoyl, mono- or diethylcarbamoyl, monocyclohexylcarbonyl, phenylcarbamoyl, dimethylcarbamoyloxy or diethylcarbamoyloxy.

Preference is given to the use according to the invention of compounds originating from the class of metal-free or metal-containing naphthalocyanines.

Emphasis should be placed on the use according to the invention of naphthalocyanines of the formula IIa (IIa)

where
$Y^1$, $Y^2$, $Y^3$, $Y^4$, $Y^5$, $Y^6$, $Y^7$ and $Y^8$, independently of one another, are each hydrogen, hydroxyl, $C_1$–$C_4$-alkyl or $C_1$–$C_{20}$-alkoxy, and
$Me^2$ is two hydrogen atoms, two lithium atoms, magnesium, zinc, copper, nickel, VO, AlCl or where $R^{19}$ is $C_1$–$C_{13}$-alkyl or $C_{10}$–$C_{20}$-alkadienyl and $Y^{20}$ and $Y^{21}$, independently of one another, are each $C_1$–$C_{13}$-alkyl or $C_2$–$C_4$-alkenyl.

Particular emphasis should be placed on the use according to the invention of naphthalocyanines of the formula IIa, where $Y^1$, $Y^2$, $Y^3$, $Y^4$, $Y^5$, $Y^6$, $Y^7$ and $Y^8$, independently of one another, are each hydroxyl or $C_1$–$C_{20}$-alkoxy, in particular $C_1$–$C_{10}$-alkoxy. The alkoxy radicals here may be identical or different.

Particular emphasis should furthermore be placed on the use according to the invention of naphthalo-cyanines of the formula IIa where $Me^2$ is two hydrogen atoms.

Emphasis should furthermore be placed on the use according to the invention of nickel dithiolene complexes of the formula III, where $L^1$, $L^2$, $L^3$ and $L^4$, independently of one another, are each phenyl, $C_1$–$C_{20}$-alkylphenyl, $C_1$–$C_{20}$-alkoxyphenyl or hydroxyl- and $C_1$–$C_{20}$-alkyl substituted phenyl, or $L^1$ and $L^2$ and $L^3$ and $L^4$ are in each case together Particular emphasis should furthermore be placed on the use according to the invention of nickel dithiolene complexes of the formula III where $L^1$ and $L^4$ are each phenyl and $L^2$ and $L^4$ are each 4-$[C_2H_5$—$C(CH_3)_2]$—$C_6H_4$.

The phthalocyanines of the formula Ia are known per se and are described, for example, in DE-B-1 073 739 or EP-A-155 780 or can be obtained by methods known per se, as used in the preparation of phthalocyanines or naphthalocyanines and as described, for example, in F. H. Moser, A. L. Thomas, "The Phthalocyanines", CRC Press, Boca Rota, Fla., 1983, or J. Am. Chem. Soc. 106 (1984), 7404 to 7410. The phthalocyanines of the formula Ib are likewise known per se and are described, for example, in EP-A-155 780 or can be obtained by the above prior-art methods (Moser, J. Am. Chem. Soc.).

The naphthalocyanines of the formula II are likewise known per se and are described, for example, in EP-A-336 213, EP-A-358 080, GB-A-2,168,372 or GB-A-2,200,650, or can be obtained by the above prior-art methods (Moser, J. Am. Chem. Soc.).

The nickel dithiolene complexes of the formula III are likewise known per se and are described, for example, in EP-A-192 215.

The aminium compounds of the formula IV are likewise known per se and are described, for example, in U.S. Pat. No. 3,484,467 or can be obtained by the methods mentioned therein.

The methine dyes of the formula V are likewise known per se and are described, for example, in EP-A-464 543 or can be obtained by the methods described therein.

The azulenesquaric acid dyes of the formula VI are likewise known per se and are described, for example, in EP-A-310 080 or U.S. Pat. No. 4,990,649 or can be obtained by the methods described therein.

Suitable solvents which can be marked according to the invention by means of the compounds described in greater detail above are, in particular, organic liquids, for example alcohols, such as methanol, ethanol, propanol, isopropanol, butanol, isobutanol, sec-butanol, pentanol, isopentanol, neopentanol and hexanol, glycols, such as 1,2-ethylene glycol, 1,2- and 1,3-propylene glycol, 1,2-, 2,3- and 1,4-butylene glycol, di- and triethylene glycol and di- and tripropylene glycol, ethers, such as methyl tert-butyl ether, 1,2-ethylene glycol mono- and dimethyl ether, 1,2-ethylene glycol mono- and diethyl ether, 3-methoxypropanol, 3-isopropoxypropanol, tetrahydrofuran and dioxane, ketones, such as acetone, methyl ethyl ketone and diacetone alcohol, esters, such as methyl acetate, ethyl acetate, propyl acetate and butyl acetate, aliphatic and aromatic hydrocarbons, such as pentane, hexane, heptane, octane, isooctane, petroleum ether, toluene, xylene, ethylbenzene, tetralin, decalin, dimethylnaphthalene, white spirit, mineral oil, such as gasoline, kerosene, diesel oil and heating oil, natural oils, such as olive oil, soya oil and sunflower oil, and natural or synthetic engine oils, hydraulic oils and transmission oils, for example vehicle engine oil and sewing machine oil, and brake fluids.

The abovementioned compounds are particularly advantageously used for marking mineral oils in which labeling is simultaneously required, for example for tax reasons. In order to keep costs of the labeling low, the usual aim is to use very dilutable dyes for the coloring. However, even dyes of high tinctorial strength cannot be detected purely visually in high dilution in mineral oils.

For this reason, it is of particular advantage to use markers which have their absorption maximum in the range from 600 to 1,200 nm and/or fluoresce in the range from 620 to 1,200 nm, since they can easily be detected using suitable instruments.

For labeling liquids, but in particular mineral oil, the abovementioned compounds are generally used in the form of solutions. Suitable solvents are preferably aromatic hydrocarbons, such as toluene and xylene. In order to avoid any excessively high viscosity of the resultant solutions, a concentration of the compound which absorbs and/or fluoresces in the IR of from 2 to 50% by weight, based on the solution, is generally selected.

The present invention furthermore provides a process for detecting markers in liquids, which comprises detecting the marker from its fluorescence in the NIR (near infrared) spectral region.

The fluorescence of the markers present in the liquids is advantageously excited by means of a semiconductor laser or a semiconductor diode. It is particularly favorable to use a semiconductor laser or a semiconductor diode having a wavelength of maximum emission in the spectral range from $\lambda_{max}$–100 nm to $\lambda_{max}$+20 nm, where $\lambda_{max}$ is the wavelength of the absorption maximum of the marker. The wavelength of maximum emission is in the range from 620 to 1,200 nm.

The fluorescence light produced in this way is advantageously detected by means of a semiconductor detector, in particular a silicon photodiode or a germanium photodiode.

Detection is particularly advantageous if the detector is preceded by an interference filter and/or a cut-off filter (with a short-wave transmission cut-off limit in the range from $\lambda_{max}$ to $\lambda_{max}$+80 nm) and/or a polarizer.

The abovementioned compounds make it very simple to detect marked liquids, even if the marker substances are only present in a concentration of approximately 0.1 ppm (detection by absorption) or approximately 5 ppb (detection by fluorescence).

The present invention furthermore provides an instrument for carrying out the process according to the invention (=detector), the detector comprising an NIR light source (semiconductor laser or semiconductor diode), one or more optical filters, an NIR polarizer and a photodetector (silicon photodiode or germanium photodiode) and, if desired, optical fibers or optical fiber bundles.

The examples below are intended to illustrate the invention in greater detail.
General procedure for detecting the markers.
I. Detection by absorption in the IR region

EXAMPLE 1

Sufficient dye of the formula was dissolved in diesel fuel to give a solution containing 1,000 ppm of dye.

This solution was diluted further in steps, and its absorption in the NIR region measured against a pure diesel fuel using a commercially available spectrometer (1 cm cell).

| Dye content in diesel fuel [ppm] | Absorption | Absorption maximum [nm] |
| --- | --- | --- |
| 100 | >>3 | — |
| 50 | 3.05 | 844.0 |
| 20 | 2.81 | 854.0 |
| 10 | 2.10 | 860.4 |
| 1 | 0.27 | 860.0 |

Similarly favorable results are achieved when naphthalocyanines of the above formula (where $R=n-C_5H_{11}$ or $n-C_{12}H_{25}$) or the dyes listed below are used for the marking.

Dye 2
Hexadecaphenylthiocopper phthalocyanine
Dye 3
Tetradecaphenylthiocopper phtahlocyanine
Dye 4
Tetradecadodecylthiocopper phthalocyanine
Dye 5

Dye 6
Hexadeca(4-tert-butylphenylthio)copper phthalocyanine
Dye 7
$NcSi[-O-Si(CH_3)_2-O-C_{12}H_{25}]_2$
Dye 8

-continued

Dye 9

Dye 10

Dyes 11 to 15

| Dye No. | L¹ | L² | L³ | L⁴ |
|---|---|---|---|---|
| 11 | 3,5-di-tert-butyl-4-hydroxyphenyl | $C_6H_5$ | 3,5-di-tert-butyl-4-hydroxyphenyl | $C_6H_5$ |
| 12 | 4-(2-methylbutan-2-yl)phenyl | $C_6H_5$ | 4-(2-methylbutan-2-yl)phenyl | $C_6H_5$ |
| 13 | $C_6H_5$ | $C_6H_5$ | $C_6H_5$ | $C_6H_5$ |
| 14 | 4-dodecylphenyl | $C_6H_5$ | 4-dodecylphenyl | $C_6H_5$ |
| 15 | bornyl | | bornyl | |

Dyes 15 to 18

| Dye No. | Z | An⊖ |
|---|---|---|
| 16 | $C_4H_9$ | $NO_3^\ominus$ |
| 17 | $C_2H_5$ | $NO_3^\ominus$ |
| 18 | $C_4H_9$ | $BF_4^\ominus$ |

Dyes 19 to 23

| Dye No. | $Q^1$ | $Q^2$ | $Q^3$ | $Q^4$ | $An^\ominus$ |
|---|---|---|---|---|---|
| 19 | $CH_3$ | $CH_3$ | Cl | Cl | $I^\ominus$ |
| 20 | $CH_3$ | $CH_3$ | H | H | $I^\ominus$ |
| 21 | $C_2H_4OCNHC(CH_3)_3$ (O=) | $C_2H_4OCNHC(CH_3)_3$ (O=) | H | H | $I^\ominus$ |
| 22 | $C_2H_4CNHC_6H_{13}$ (O=) | $C_2H_4CNHC_6H_{13}$ (O=) | H | H | $ClO_4^\ominus$ |
| 23 | $C_3H_6SO_3^\ominus$ | $C_3H_6SO_3H$ | H | H | Betain |

Dye 24

II. Detection by fluorescence in the NIR region

Figure 1:
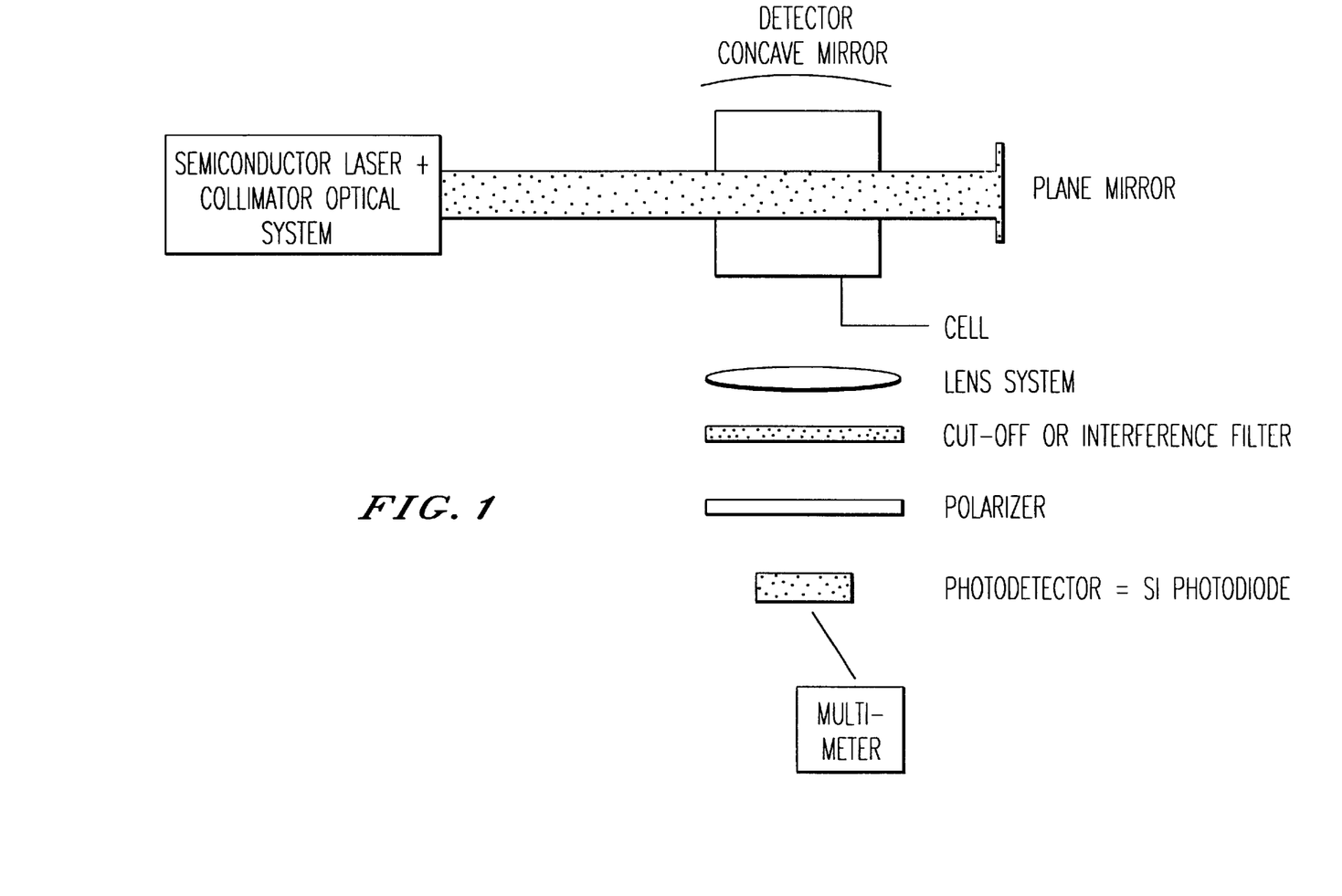
FIG. 1 shows a diagrammatic structure of a detector.

FIG. 1 shows the diagrammatic structure of the detector.

The marker fluorescence is excited using the emission from a commercial semiconductor diode laser. The parallel laser beam is shone onto the sample in a 1 cm cell. In order to double the excitation intensity, the transmitted light beam is reflected by a mirror and again shone through the sample.

The fluorescence light is imaged by means of optical elements (lens system) onto the detector, a silicon photodiode. The light emitted at the rear is likewise thrown onto the silicon photodiode by a concave mirror.

In order to separate the unwanted light (scattered excitation light) from the fluorescence light, cut-off and/or interference filters and/or a polarizer (NIR polarization foil) are used.

The optimization of the polarizer is selected so that the direction of maximum transmission is perpendicular to the polarization plane of the excitation light.

EXAMPLE 25

Sufficient dye of the formula $R = n\text{-}C_4H_9$ was dissolved in diesel fuel to give a stock solution containing 219 ppb of dye. Further solutions were prepared therefrom by dilution with diesel fuel.

These solutions were measured in accordance with general procedure II using the following equipment settings.

Excitation: GaAlAs semiconductor diode laser having a wavelength of 813 nm; CW output 7 mW.

Filter: Long-pass interference filter 850 nm (Corion). Photodetector: Silicon photodiode having an area of 1 cm² (UDT). The photocurrent was measured using a current/voltage converter (UDT, model 350).

The results are shown in the table below.

| Dye content in the diesel fuel [ppb] | Absorbance at $\lambda_{max}$ | Fluorescence signal (in scale units) |
|---|---|---|
| 219 | 0.05 | 2366 |
| 43.7 | 0.01 | 451 |
| 8.75 | 0.002 | 106 |
| 1.75 | 0.0004 | 40 |
| 0 | 0.0 | 20 |

This gives a lower detection limit for the marker by fluorescence of about 5 ppb.

Similarly favorable results are achieved when naphthalocyanines of the above formula (where R=n–$C_5H_{11}$ or n–$C_{12}H_{25}$) or the dyes listed below are used for the marking.

(R = t-$C_4H_9$)

Dye 26
Me = 2H

Dye 27
Me = Zn

Dye 28
Me = AlCl

Dye 29
NcSi[—O—Si($CH_3$)$_2$—O—$C_{12}H_{25}$]$_2$

Dye 30

Dye 31

Dye 32

-continued

Dye 33

Dye 34

Dye 35 to 37

| Dye No. | Z | An⊖ |
|---|---|---|
| 35 | C$_4$H$_9$ | NO$_3^\ominus$ |
| 36 | C$_2$H$_5$ | NO$_3^\ominus$ |
| 37 | C$_4$H$_9$ | BF$_4^\ominus$ |

Dyes 38 to 42

| Dye No. | Q$^1$ | Q$^2$ | Q$^3$ | Q$^4$ | An⊖ |
|---|---|---|---|---|---|
| 38 | CH$_3$ | CH$_3$ | Cl | Cl | I$^\ominus$ |
| 39 | CH$_3$ | CH$_3$ | H | H | I$^\ominus$ |
| 40 | C$_2$H$_4$OCNHC(CH$_3$)$_3$ (C=O) | C$_2$H$_4$OCNHC(CH$_3$)$_3$ (C=O) | H | H | I$^\ominus$ |
| 41 | C$_2$H$_4$CNHC$_6$H$_{13}$ (C=O) | C$_2$H$_4$CNHC$_6$H$_{13}$ (C=O) | H | H | ClO$_4^\ominus$ |
| 42 | C$_3$H$_6$SO$_3^\ominus$ | C$_3$H$_6$SO$_3$H | H | H | Betain |

Dye 43

[structure with two indoline groups connected via CH=CH–(chlorocyclohexene)–CH=CH, anion I$^\ominus$]

We claim:

1. A method of identifying a liquid comprising the sequential steps of:
   i) detecting a marker compound in a liquid; and
   ii) identifying said liquid based on the identity of said marker compound, wherein said marker compound is selected from the group consisting of a metal-free phthalocyanine, a metal-containing phthalocyanine, a metal-free naphthalocyanine, a metal-containing naphthalocyanine, a nickel dithiolene complex, an aminium compound of an aromatic amine, a methine dye, an azulenesquaric acid dye and a mixture thereof, wherein said marker compound has an absorption maximum in the range of from 600 to 1,200 nm and/or a fluroescence maximum in the range of from 620 to 1,200 nm.

2. A method as claimed in claim 1, wherein the compound comes from the class of metal-free or metal-containing naphthalocyanines or nickel dithiolene complexes.

3. A method as claimed in claim 1, wherein the compound comes from the class of metal-free or metal-containing naphthalocyanines.

4. The method of claim 1, further comprising adding said marker compound of a known identity to said liquid of a known identity, prior to step i).

5. The method of claim 1, wherein the identity of said liquid is uncertain at step i).

6. A method as claimed in claim 1, wherein the marker is detected from its fluorescence in the NIR spectral region.

7. A method as claimed in claim 6, wherein the fluorescence is excited by means of a semiconductor laser or a semiconductor diode.

8. A method as claimed in claim 6, wherein the fluorescence light is detected by means of a semiconductor detector.

9. A method as claimed in claim 6, wherein a semiconductor laser or a semiconductor diode having a wavelength of maximum emission in the spectral range from $\lambda_{max}-100$ nm to $\lambda_{max}+20$ n is used, where $\lambda_{max}$ is the wavelength of the absorption maximum of the marker.

10. A method as claimed in claim 6, wherein a semiconductor laser or a semiconductor diode having a wave-length of maximum emission of from 620 to 1,200 nm is used.

* * * * *